(12) United States Patent
Kusagawa et al.

(10) Patent No.: US 7,048,726 B2
(45) Date of Patent: May 23, 2006

(54) ABSORBENT ARTICLE

(75) Inventors: Tetsuya Kusagawa, Tochigi (JP); Atsushi Murai, Tochigi (JP); Mitsugu Hamajima, Tochigi (JP); Jinko Noguchi, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/056,485

(22) Filed: Jan. 28, 2002

(65) Prior Publication Data

US 2002/0157771 A1 Oct. 31, 2002

(30) Foreign Application Priority Data

Jan. 29, 2001 (JP) ............................. 2001-019330
Dec. 13, 2001 (JP) ............................. 2001-380693

(51) Int. Cl.
A61F 13/15 (2006.01)
A61F 13/20 (2006.01)

(52) U.S. Cl. ......................... 604/385.28; 604/385.03; 604/387

(58) Field of Classification Search ............... 604/380, 604/385.22, 385.24–385.29, FOR. 104, 385.03, 604/387

See application file for complete search history.

(56) References Cited

U.S. PATENT DOCUMENTS

| | | | | |
|---|---|---|---|---|
| 4,081,301 A | * | 3/1978 | Buell | 156/164 |
| 4,397,645 A | * | 8/1983 | Buell | 604/380 |
| 4,640,859 A | * | 2/1987 | Hansen et al. | 428/105 |
| 4,695,278 A | * | 9/1987 | Lawson | 604/385.27 |
| 5,312,386 A | * | 5/1994 | Correa et al. | 604/379 |
| 5,340,648 A | * | 8/1994 | Rollins et al. | 428/343 |
| 5,407,438 A | * | 4/1995 | Hedlund et al. | 604/385.26 |
| 5,476,458 A | * | 12/1995 | Glaug et al. | 604/378 |
| 5,769,835 A | * | 6/1998 | Fell et al. | 604/385.28 |
| 6,159,191 A | * | 12/2000 | Mishima et al. | 604/385.28 |
| 6,506,187 B1 | * | 1/2003 | Andersson et al. | 604/385.28 |
| 6,514,234 B1 | * | 2/2003 | Shimizu et al. | 604/385.27 |
| 6,569,140 B1 | * | 5/2003 | Mizutani et al. | 604/385.28 |
| 6,624,340 B1 | * | 9/2003 | Mizutani et al. | 604/358 |
| 6,706,029 B1 | * | 3/2004 | Suzuki et al. | 604/385.28 |
| 2002/0062116 A1 | * | 5/2002 | Mizutani et al. | 604/385.28 |
| 2002/0064624 A1 | * | 5/2002 | Mizutani et al. | 428/126 |
| 2002/0128626 A1 | * | 9/2002 | Friderich et al. | 604/385.28 |

(Continued)

FOREIGN PATENT DOCUMENTS

EP 0 346 477 A 12/1989

(Continued)

OTHER PUBLICATIONS

U.S. Appl. No. 60/342,938.*

(Continued)

*Primary Examiner*—Karin Reichle
(74) *Attorney, Agent, or Firm*—Birch, Stewart, Kolasch & Birch, LLP (57) ABSTRACT

An absorbent article (1) having a liquid-retentive absorbing layer (2), a liquid-impermeable leakproof layer (3), and standing gathers (4) on each side. The gathers have an elastically extensible portion (40) coming into planar contact with the wearer's skin while worn. The elastically extensible portion (40) is made of a sheet (44) and at least one elastic member (45), the elastic member (45) being fixed to the sheet (44) discretely in the longitudinal direction in its stretched state, and the parts of the sheet where the elastic member (45) is not fixed are raised by contraction of the elastic member (45) to form a plurality of hollow ridges (43) on the side of the elastically extensible portion (40) to be brought into contact with the wearer's skin.

2 Claims, 5 Drawing Sheets

U.S. PATENT DOCUMENTS

| | | | |
|---|---|---|---|
| 2003/0120247 A1* | 6/2003 | Miyamoto | 604/385.27 |
| 2003/0120248 A1* | 6/2003 | Miyamoto | 604/385.28 |
| 2004/0002690 A1* | 1/2004 | Miyamoto | 604/385.25 |

FOREIGN PATENT DOCUMENTS

| | | | |
|---|---|---|---|
| EP | 0 925 768 A | | 6/1999 |
| EP | 1 101 476 A | | 5/2001 |
| EP | 1 166 728 A | | 1/2002 |
| EP | 1 208 826 A | | 5/2002 |
| GB | 2296445 A | * | 7/1996 |
| GB | 2319730 A | * | 6/1998 |
| JP | 03090149 A | * | 4/1991 |
| JP | 2001-145667 | | 5/2001 |
| WO | WO 9508972 A1 | * | 4/1995 |
| WO | 98 37838 A | | 9/1998 |
| WO | WO 9916398 A1 | * | 4/1999 |

OTHER PUBLICATIONS

U.S. Appl. No. 60/392,895.*

U.S. Appl. No. 60/392,896.*

European Search Report.

* cited by examiner

ABSORBENT ARTICLE

BACKGROUND OF THE INVENTION

The present invention relates to absorbent articles, such as sanitary napkins, incontinence pads, and panty liners, which have elastically extensible portions coming into planar contact with the wearer's skin.

Absorbent articles with standing gathers, such as sanitary napkins, in which the standing gathers have an elastically extensible portion providing a planar contact with the wearer's skin are known.

However, the standing gathers of conventional absorbent articles do not always feel comfortable to a wearer, rather feeling stiff or providing poor cushioning properties. The feel of standing gathers could be improved by, for example, adjusting the number of the elastic members to be disposed or extensibility of the elastic members. It is difficult nevertheless to achieve desired improvement without impairing the merits of a planar contact, such as a good fit and leakproofness. In addition, conventional elastically extensible portions tend to fail to keep their planar shape stably. They are liable to bunch up or contract in an undesired direction while in use, so that improvements in fit and leakproofness are not obtained.

SUMMARY OF THE INVENTION

An object of the present invention is to provide an absorbent article with standing gathers, such as a sanitary napkin, an incontinence pad, and a panty liner, in which the standing gathers surely have soft ridges on the wearer's skin contact side to provide a comfortable feel while retaining a good fit and excellent leakproofness.

Another object of the present invention is to provide an absorbent article with standing gathers, such as a sanitary napkin, an incontinence pad, and a panty liner, in which the elastically extensible portions of the standing gathers coming into contact with the wearer's skin feel comfortable and have excellent planar shape retention to assure a good fit and excellent leakproofness.

The object of the present invention is accomplished by an absorbent article having a liquid-retentive absorbing layer, a liquid-impermeable leakproof layer, and standing gathers on each side thereof which have an elastically extensible portion coming into planar contact with the wearer's skin while worn, wherein the elastically extensible portion is made of a sheet and at least one elastic member, the elastic member being fixed to the sheet discretely in the longitudinal direction thereof in their stretched state, and the parts of the sheet where the elastic member is not fixed are raised by contraction of the elastic member to form a plurality of hollow ridges on the side of the elastically extensible portion to be brought into contact with the wearer's skin in a linear manner along the contraction direction of the elastic member, the hollow ridges each extending across the contraction direction of the elastic member (hereinafter referred to as a first aspect of the invention).

The object of the present invention is also accomplished by an absorbent article having a substantially oblong shape and comprising a liquid-retentive absorbing layer, a liquid-impermeable leakproof sheet, and standing gathers which are provided on each longer side thereof and have an elastically extensible portion coming into planar contact with the wearer's skin while worn, wherein the elastically extensible portion is made of a fiber aggregate containing at least one elastic member and has a large number of ridges formed on its side to be brought into contact with the wearer's skin across the width thereof, the fiber aggregate forming the ridges having a lower density than that forming valleys between every adjacent ridges (hereinafter referred to as a second aspect of the invention).

BRIEF DESCRIPTION OF THE DRAWINGS

The present invention will be more particularly described with reference to the accompanying drawings, in which.

DETAILED DESCRIPTION OF THE PREFERRED EMBODIMENTS

Figure 1:
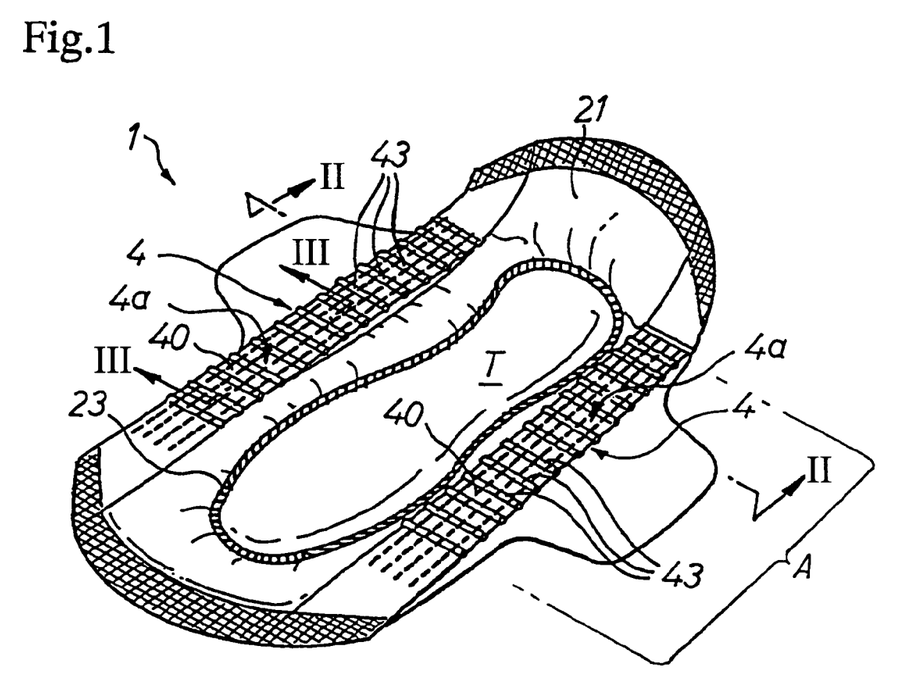
FIG. 1 is a perspective view of a sanitary napkin as an embodiment of the first aspect of the invention.
Figure 2:
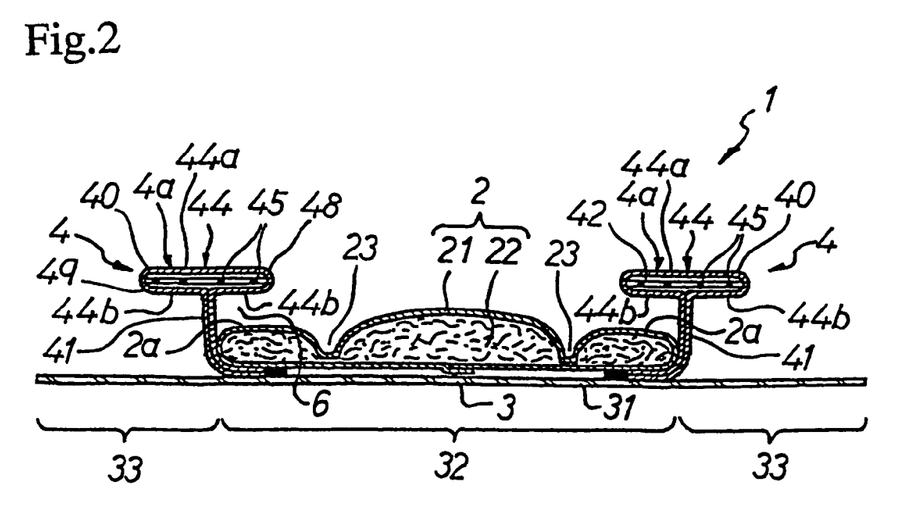
FIG. 2 is a cross sectional view of FIG. 1, taken along line II—II.
Figure 3:
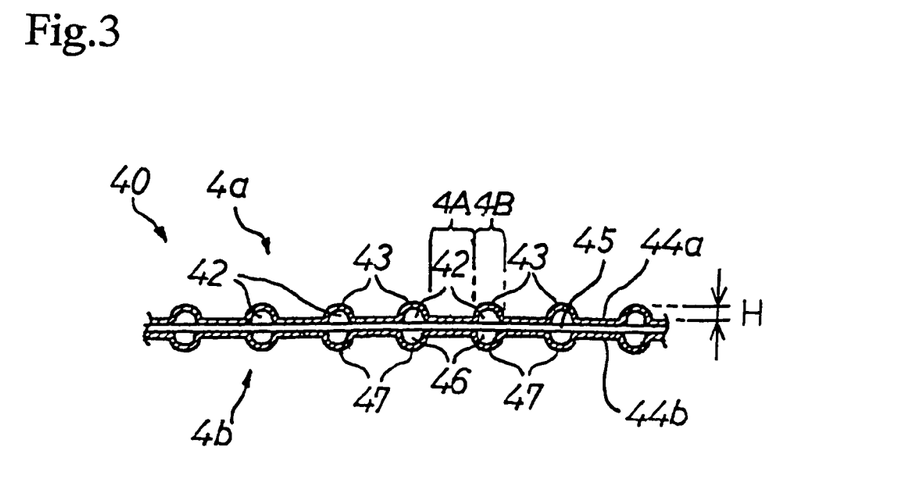
FIG. 3 is a longitudinal sectional view of FIG. 1, taken along line III—III.

FIGS. 1 through 3 illustrate a sanitary napkin 1 as one embodiment of the first aspect of the invention, which is substantially oblong and has a liquid-retentive absorbing layer 2, a liquid-impermeable leakproof layer 3, and standing gathers 4. The standing gathers 4 on each side have an elastically extensible portion 40.

The absorbing layer 2 has a rectangular shape with arched ends in its plan view. It is composed of a liquid-permeable topsheet 21, which provides the upper side 2a of the absorbing layer 2, and a liquid-retentive absorbent member 22 which is disposed under the topsheet 21 and absorbs and retains liquid having passed through the topsheet 21.

The leakproof layer 3 is formed of a liquid-impermeable backsheet 31. It has a main region 32 whose shape is almost the same as the absorbing layer 2 and a pair of wings 33 extending from both longer sides of the main region 32. The absorbing layer 2 is fixed to the main region 32 by known bonding means, such as an adhesive. A pressure-sensitive adhesive (not shown) is applied to the back side of the main region 32 and the wings 33, with which to be fixed to a garment.

The standing gathers 4 serve as a guard blocking flows of urine, soft stools, menstrual blood, etc. to prevent leaks. As shown in FIG. 1, the standing gathers 4 are provided along both longer sides of the napkin 1, more specifically along both longer sides of the absorbing layer 2. The standing gathers 4 on each side have an elastically extensible portion 40 which comes into planar contact with the wearer's skin while worn. The elastically extensible portions 40 show extensibility in its longitudinal direction and come into planar content with the wearer's skin while worn over the length corresponding to a discharge spot area T (the part of the absorbing layer 2 that faces the discharging part of a wearer).

The standing gathers 4 in this embodiment stand from near the longer side edge of the absorbent member 22 and are composed of an elastically extensible portion 40 and an upright portion 41. The upright portion 41 connects integrally to the lower side (the side not brought into contact with a wearer) of the elastically extensible portion 40 at the upper end thereof and is fixed at the lower end thereof to near the longer side edge of the absorbing layer 2.

The standing gathers 4 on each side have a T-shaped vertical profile as shown in FIG. 2. The elastically extensible portion 40 has an inward extension 48 and an outward extension 49 which extend inwardly and outwardly, respectively, from the middle corresponding to the upper end of the upright portion 41. The inward extension 48 and the outward extension 49 extend substantially horizontally so that their upper sides are on substantially the same plane. The inward and outward extensions 48 and 49 have almost the same width.

Each elastically extensible portion 40 has a large number of hollow ridges 43 (having an empty space 42) which are regularly arranged on its wearer's skin contact side. The ridges 43 are equally spaced along the longitudinal direction of the elastically extensible portion 40 and in parallel to each other and across the elastically extensible portion 40 as shown in FIG. 1.

Figure 4:
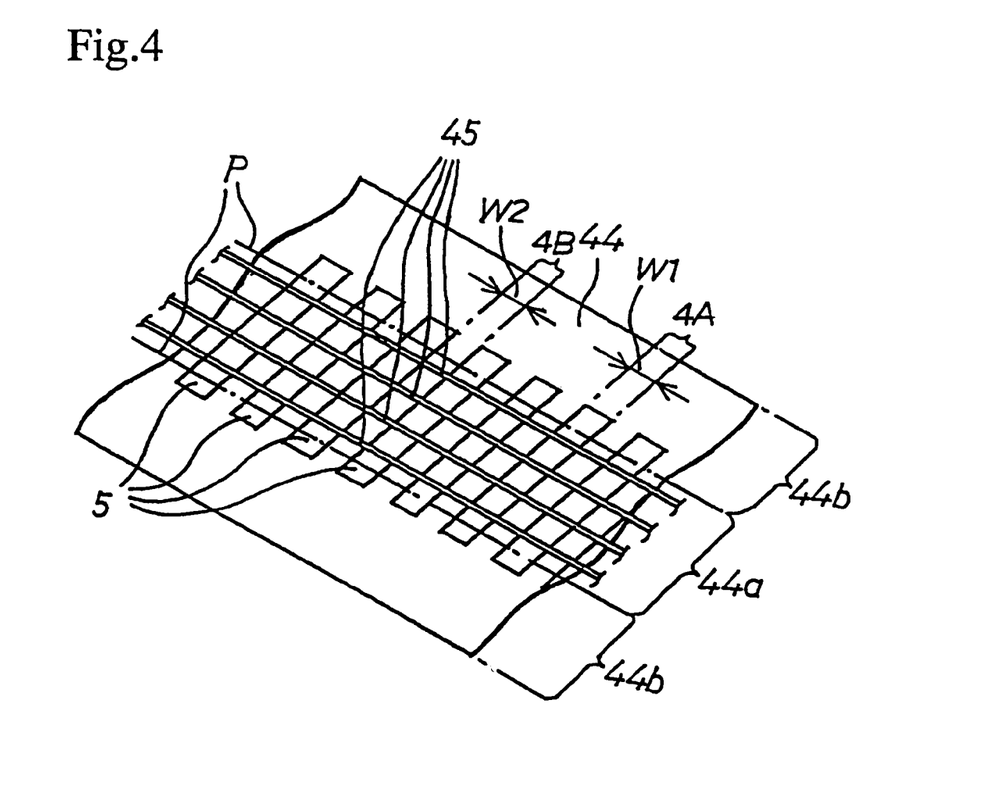
FIG. 4 is a perspective view showing the step of fixing elastic members in their stretched state to a sheet to make an elastically extensible portion.

The elastically extensible portion 40 is fixed at its both shorter side ends to the shorter side ends of the napkin 1. As shown in FIGS. 3 and 4, the elastically extensible portion 40 is made of a sheet 44 and a plurality of elastic members 45 discretely bonded to the sheet 44 in their stretched state so that sheet 44/elastic member 45 joint areas 4A and non-joint areas 4B alternate. The ridges 43 according to the present embodiment are formed of the non-joint areas 4B of the sheet 44 rising as a result of contraction of the elastic members 45.

The standing gathers 4 according to the present embodiment are formed by fixing, to a prescribed part of a sanitary napkin, an elastically extensible member prepared by bonding a plurality of elastic members 45 in their stretched state to the sheet 44 via an adhesive 5 discretely applied to the sheet 44 at given intervals as shown in FIG. 4.

More specifically, the sheet 44 used to make the standing gathers 4 is divided in three sections; a middle section 44a with a prescribed width and two sections 44b which extend from the longitudinal sides of the middle section 44a as shown in FIGS. 2 and 4. The middle section 44a forms the skin contact side 4a of the elastically extensible portion 40. The sections 44b are folded back along folding lines P to envelope the elastic members 45, forming the reverse side of the elastically extensible portion 40 that is not brought into contact with the wearer's skin. The sections 44b join together on this side and further extend downward to form the upright portion 41.

The elastic members 45 are also bonded discretely with the folded parts of the sections 44b in the same manner as bonded to the middle section 44a. As a result, the elastically extensible portion 40 also has on its reverse side (the side not brought into contact with the wearer's skin) a large number of hollow ridges 47 (having an empty space 46) which are parallel to each other at certain intervals and across the elastically extensible portion 40. The ridges 43 on the wearer's skin contact side 4a and the ridges 47 on the opposite side 4b are symmetrical about the plane having the elastic members 45.

For ensuring a comfortable feel of the elastically extensible portion 40 and/or further improving planar shape retention of that portion, it is preferred for the joint areas 4A where the sheet 44 and the elastic members 45 are joined to have a width W1 (see FIG. 4) of 0.5 to 10 mm, particularly 1 to 5 mm and for the non-joint areas 4B where the sheet 44 and the elastic members 45 are not joined to have a width W2 (i.e., interval of the joint areas 4A) of 1 to 20 mm, particularly 2 to 10 mm.

For making standing gathers 4 with fit and cushioning softness and for securing shape stability of the elastically extensible portion 40 widthwise, it is preferred for the ridges 43 to have an average length of 3 to 50 mm, particularly 10 to 30 mm, across the elastically extensible portion 40 and an average height H (see FIG. 3) of 0.5 to 10 mm, particularly 1 to 5 mm. Where the ridges 43 are parallel with the width direction of the elastically extensible portion 40, the "length" of the ridges are the real length. Where the ridges 43 are not parallel with the width direction of the elastically extensible portion 40, the "length" of the ridges as referred to here is a length of the ridges as projected on a line parallel to the width direction.

For securing the fit and cushioning properties of the standing gathers and the widthwise stability of the elastically extensible portion 40, the length of the ridges is preferably 30% or more, still preferably 50 to 100%, of the width of the elastically extensible portion 40. The empty spaces 42 and 46 of the hollow ridges preferably have a cross-sectional area of 0.3 to 130 mm$^2$, particularly 1 to 50 mm$^2$, for securing cushioning properties, fit, and softness.

The napkin 1 according to the present embodiment has an anti-leak channel 23 of prescribed shape formed on the topsheet 21 side of the absorbent member 22. The anti-leak channel 23 forms a loop in its plan view. In detail, the loop is nearly elliptical with its major axis in the longitudinal direction of the napkin 1. The part of the loop in a discharging part-facing section A shown in FIG. 1 (when the napkin 1 is crosswise divided into three sections, the discharging part-facing section A is the middle section which faces the discharging part of a wearer and includes the aforementioned discharge spot area T) is curved inward. The anti-leak channel 23 is formed by compressing the topsheet 21 and the absorbent member 22.

It is preferred that at least the part of the inward extension 48 that is located on both sides of the discharging part-facing section A, especially on both sides of the discharge spot area T, be above the absorbent member 22 so that this part of the inward extension 48 and the upright portion 41 can form a pocket 6 as shown in FIG. 2. Blood flowing laterally along the wearer's skin is kept back in this pocket and, meanwhile, quickly absorbed by the absorbent member 22. That is, the barrier effect of the standing gathers 4 and the absorbing effect of the absorbent member 22 exert enhanced leakproofing effects in good cooperation.

It is also preferred that at least the part of the inward extension 48 that is located on both sides of the discharging part-facing section A, especially on both sides of the discharge. spot area T, be farther from the center of the absorbent member 22 than the anti-leak channel 23. In this configuration, the anti-leak channel 23 can serve as a hinge at which the part of the absorbent member 22 outside the channel 23 and along the longer sides of the napkin 1 may be bent downward in conformity to the contour of a wearer's body. As a result, a wearer can get a perfect fit with the sanitary napkin 1 and enjoy the elastic planar sealing effect of the upper side of the elastically extensible portion 40 (both the inner and outer extensions 48 and 49). Further, even when the standing gathers 4 are collapsed under a pressure, liquid is guided by the channel 23 along the longitudinal direction of the napkin and hardly reaches the standing gathers 4. Even if liquid reaches the standing gathers 4, it is trapped by the absorbent member 22 existing there and prevented from overflowing across the standing gathers 4. In general, if upstanding gathers are stained with even a small amount of blood, a wearer is likely to feel that the whole napkin has been soiled badly so that the napkin should be changed notwithstanding a sufficient absorbing capacity left. Such an uneconomical use can be avoided with the above-described configuration because blood is prevented from reaching the standing gathers 4 by the guiding effect of the anti-leak channel 23.

In the present embodiment, each of the inner extension 48 and the outer extension 49 is provided with a plurality of elastic members 45 along the length thereof. The inner and the outer extensions have substantially the same extensibility. Even in a situation that the standing gathers 4 easily fall inward with some wearer's movements, the elastic members 45 disposed in the outer extension 49 exert a tension to provide a force for inclining the standing gathers 4 outward. Therefore, to dispose elastic members 45 in both the inner and the outer extensions 48 and 49 is effective to prevent the standing gathers 4 from falling inward. The planar contact of the elastically extensible portion 40 with the skin can thus be maintained.

The sanitary napkin 1 will be described from the aspect of material. The topsheet 21, the absorbent member 22, the backsheet 31, and the sheet 44 and the elastic members 45 for making the elastically extensible portion 40 can be of any materials customarily employed in this type of absorbent articles such as sanitary napkins.

In particular, materials of the sheet 44 for making the elastically extensible portion include nonwoven fabrics, films, and combinations thereof that have been used in conventional sanitary absorbent articles. Taking into consideration the soft touch of the elastically extensible portion and the cushioning and leakproofing effects of the standing gathers, water-repellent and water-resistant nonwoven materials are preferably used.

Suitable examples include nonwoven fabrics made of polyethylene, polypropylene, polyester or combinations thereof by carding, spun bonding, melt blowing or like methods. Weight being put on feel, suction heat bonded nonwoven fabric is preferred, which is prepared by applying hot air to a fiber web obtained by carding. Weight put on water resistance, spun-bonded nonwoven fabric or SMS (spunbond-meltblown-spunbond) nonwoven fabric is preferred.

Taking surface softness and water resistance into consideration, nonwoven fabric made of fibers having a fineness of 3 dtex or smaller is preferred. In order to assure shape stability of the elastically extensible portion 40 in its width direction and to form the ridges stably, nonwoven fabric having been embossed is preferably used as well.

Any extensible materials can be used as an elastic member 45 for making the elastically extensible portion 40. Such materials include strings, strips or films of polyurethane, natural rubber, polybutadiene rubber, etc. For the time being, rubbery strings are preferably used as arranged in parallel from considerations of cost and residual strain in extension. Where a plurality of elastic strings are used, they are preferably equally spaced in the width direction of the elastically extensible portion 40 as in the napkin 1 of the present embodiment. It is particularly preferred to decide the interval and the number of the elastic members 45 so that ridges 43 may be formed over the whole width of the elastically extensible portion 40.

The sanitary napkin 1 according to the present embodiment can be used as attached to a prescribed position of underwear as is usual with conventional sanitary napkins.

In the sanitary napkin 1 of the present embodiment, the elastically extensible portion 40 feels soft and smooth, and the standing gathers 4 have an excellent cushioning effect, owing to the hollow ridges on its skin contact side 4a. Therefore, the standing gathers feel very comfortable to a wearer, and the ridges are easily deformed in conformity to the wearer's body contour, which is not flat, and the wearer's movement, making no gaps with the wearer's skin. Since it is unnecessary to greatly reduce the extension stress of the elastic members in an effort to assure a good feel and comfortable wearability, the effects of the elastically extensible portion providing a planar content with the wearer's skin in improving fit and leakproofness are not impaired.

Having a large number of ridges 43 on the skin contact side 4a of the elastically extensible portion 40, each extending in the width direction of the napkin 1, the elastically extensible portion 40 exhibits excellent flat shape retention and easily curves in the longitudinal direction thereof to provide a comfortable fit and high leakproofness. That is, since the plane of the elastically extensible portion has a large number of transverse ridges arranged in the longitudinal direction, the elastically extensible portion has increased shape stability (firmness) in the width direction, while the joint areas 4A between the ridges serve as flexible parts for curving lengthwise. As a result, the elastically extensible portion is capable of curving lengthwise along the contour of the wearer's crotch while retaining its plane in the width direction without bunching under an inward compressive force from the thighs, whereby a good fit to the wearer's body is provided to produce an excellent leakproofing effect.

Because the ridges 43 are formed upon contraction of the elastic members 45 and the resultant rise of the sheet 44 in the non-joint areas 4B, an elastically extensible member making the elastically extensible portion 40 can be transferred flat with the elastic members 45 extended on the production line of the napkins 1. The elastic members 45 are relaxed in the final products to surely form the ridges. The absorbent articles such as the sanitary napkins 1 are usually packaged as compressed so that the ridges 43 may be collapsed in the package but are surely restored on use.

Since the upright portion 41 of the standing gathers 4 connects to the middle of the width of the elastically extensible portion 40, the standing gathers 4 are hardly pressed down as compared with otherwise designs, for example, the designs shown in FIG. 9 and thus secure a better fit and leakproofness stably.

Figure 5:
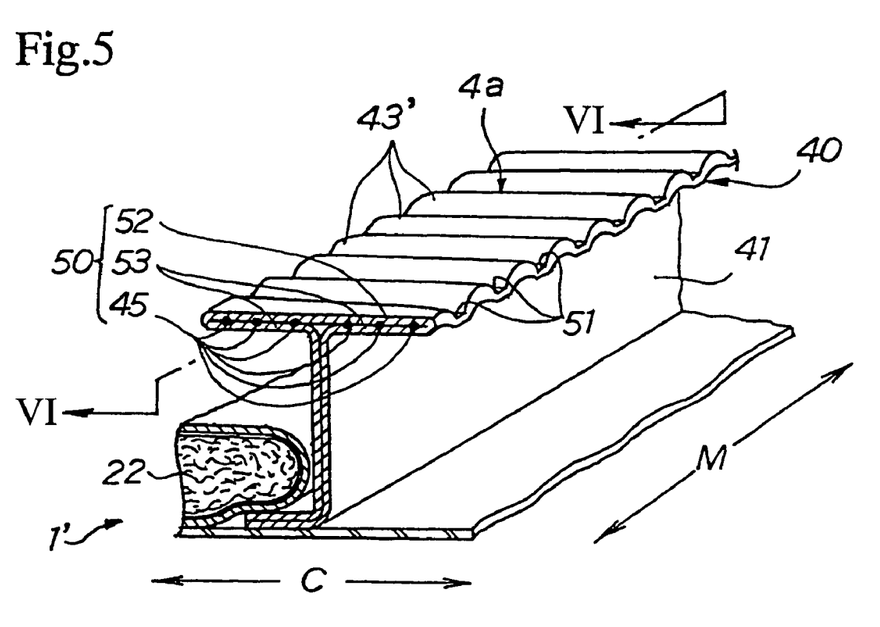
FIG. 5 is a partial perspective view of a sanitary napkin as an embodiment of the second aspect of the invention.
Figure 6:
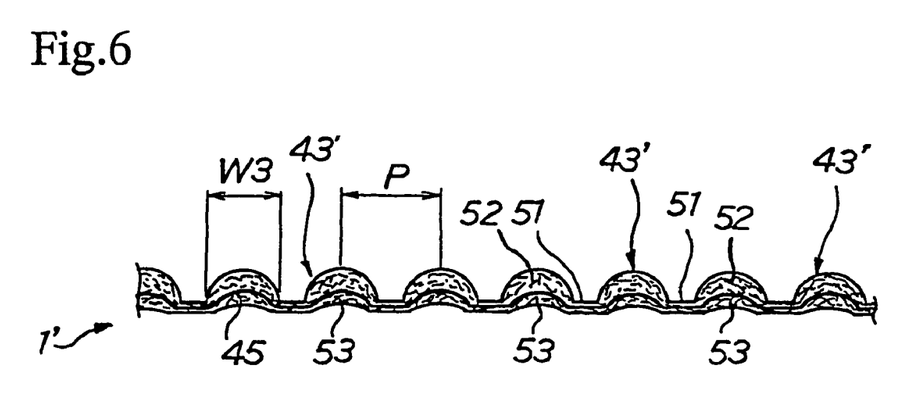
FIG. 6 is a longitudinal sectional view of FIG. 5, taken along VI—VI line.

FIGS. 5 and 6 illustrate a sanitary napkin 1' as one embodiment of the second aspect of the present invention. The sanitary napkin 1' will be described with respect to differences from the sanitary napkin 1 according to the first aspect of the invention. Otherwise the description about the latter applies to the former.

As shown in FIGS. 5 and 6, the elastically extensible portion 40 of the sanitary napkin 1' is made of a fiber aggregate 50 containing elastic members 45. The elastically extensible portion 40 has, on the skin contact side 4a thereof, a large number of raised parts, i.e., ridges 43' which are spaced, regularly arranged, and across the width (in direction C indicated in FIG. 5).

The density of the fiber aggregate 50 in the ridges 43' is lower than that in the depressed parts, i.e., valleys 51 between every adjacent ridges 43'. With a relatively lower density, the ridges 43' are flexibly deformable under the wearer's body pressure to give an excellent feel and comfort while worn. At the valleys 51 having a relatively higher density, the elastic members 45 and the fiber aggregate 50 are securely united together to assure shape stability of the ridges without impairing the feel or comfort. As a result, the elastically extensible portion 40 exhibits improved planar shape retention and thereby provides an excellent fit and high leakproofness.

Having a reduced density, the ridges 43' will reduce in contact area with the skin, not allowing liquid to spread between the skin and the ridges. On the other hand, the fiber aggregate in the valleys 51 has increased resistance against liquid pressure due to its increased density so that liquid is prevented from spreading in the elastically extensible portion to improve the anti-leakage effect.

The fiber aggregate 50 used in the sanitary napkin 1' according to this particularly embodiment is composed of two fiber aggregate layers 52 and 53 and six elastic members 45 of string form. Both the fiber aggregate layers 52 and 53 protrude on the same side in the thickness direction of the elastically extensible portion 40, i.e., toward the wearer's skin. Having elastic members sandwiched between the two wavy fiber layers, the ridges and valleys have increased shape retention under pressure. The lower-density protrusions and the higher-density depressions of the upper fiber layer and those of the lower fiber layer are superposed respectively to enhance the above effects, i.e., the feel, fit, and leakproofness.

The densities of the fiber aggregate 50 in the ridges 43' and the valleys 51 are measured as follows. A 10 mm wide and 50 mm long test piece is cut out of the elastically extensible portion in its relaxed state, with the length agreeing with the extensible direction i.e., direction M in FIG. 5, and the width agreeing with the direction perpendicular to the extensible direction, i.e., direction C in FIG. 5. The length of the test piece fixed at 50 mm, the cut area is enlarged under a microscope (SZH-1LAB, supplied by Olympus Optical Co., Ltd.), and the thicknesses of the ridges and the valleys are measured. The basis weight of the fiber aggregate before being shaped into the elastically extensible portion (the basis weight of the test piece) is measured. The density of each part is calculated from equation:

Density (g/cm$^3$)=basis weight of test piece/thickness

Where the fiber aggregate 50 is composed of the two layers 52 and 53 as in this particular embodiment, the thicknesses of each fiber layer are measured at the ridges and the valleys, and the density of each part is calculated from the total thickness of each part and the total basis weight of the two layers (the basis weight of the test piece) according to the same equation.

It is preferred that the density of the fiber aggregate 50 in the ridges 43' be 0.005 to 0.3 g/cm$^3$, particularly 0.01 to 0.2 g/cm$^3$, for obtaining a satisfactory feel. It is preferred that the density in the valleys 51 be 0.01 to 0.3 g/cm$^3$, particularly 0.02 to 0.3 g/cm$^3$, for obtaining shape stability.

The elastic members 45 are disposed between the two fiber aggregate layers 52 and 53. The fiber aggregate 50 has been embossed to have compressed parts and non-compressed parts, or weakly compressed parts that have been compressed under a weaker pressure than imposed to form the compressed parts, alternately. The non-compressed parts or the weakly compressed parts correspond to the ridges 43', and the alternating compressed parts correspond to the valleys 51.

Figure 7A:
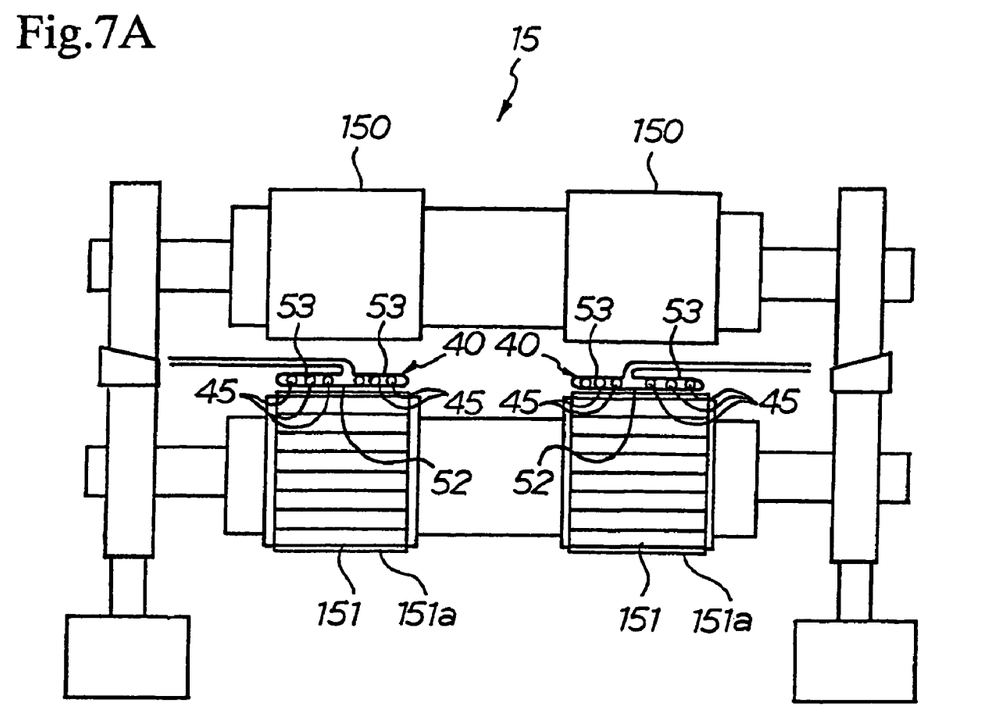
FIG. 7A is a schematic front view of an embossing means, and FIG. 7B schematically shows a fiber aggregate being embossed by the embossing means of FIG. 7A.
Figure 7B:
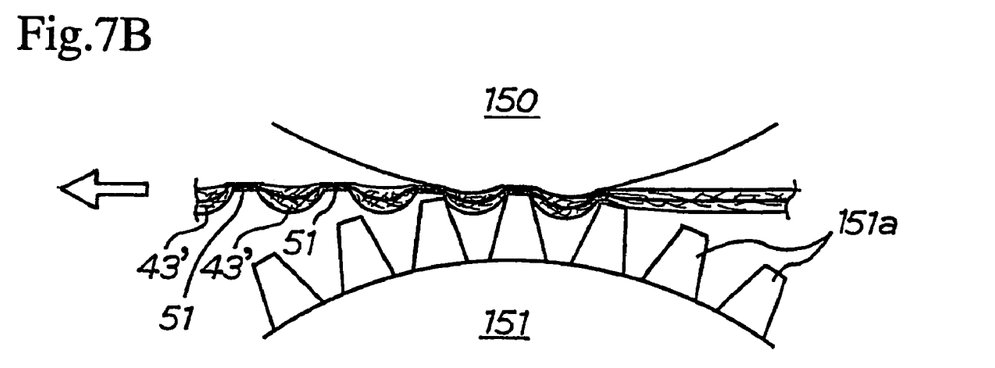

In FIGS. 7A and 7B is shown an embossing means 15 used to carry out the embossing. The embossing means 15 has an anvil roll 150 having elasticity on its circumference surface and a rigid embossing roll 151 with ridges 151a radially arrayed on its circumference surface as shown in FIG. 7B. At least the surface of the anvil roll 150 is preferably made of an elastic material such as silicone rubber.

In order to stabilize the raised/depressed shape and to secure fixing of the elastic members, it is preferred that the two fiber aggregate layers 52 and 53 be thermally fused together in the compressed parts, i.e., the valleys 51. While the fiber layer 52 and the fiber layer 53 used in the present embodiment are formed by folding a continuous sheet as depicted in FIGS. 5 and 7A, they may be made of separate sheets.

Figure 8:
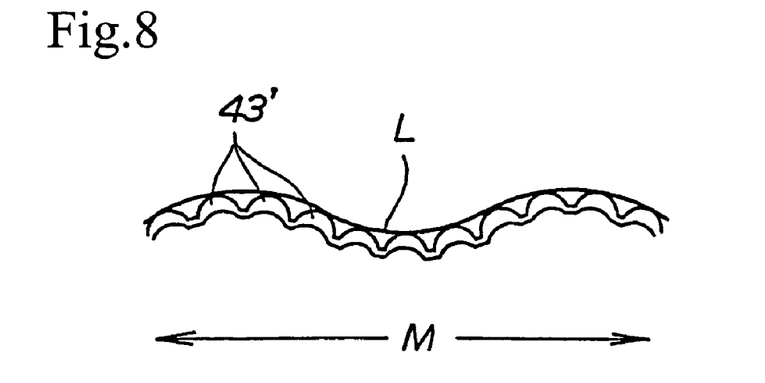
FIG. 8 schematically illustrates the wavy line connecting the apices of the ridges in a longitudinal section of the elastically extensible portion.

As shown in FIG. 8, the elastically extensible portion 40 of the sanitary napkin 1' according to the present embodiment shows a curved section taken along the lengthwise direction (direction M in FIG. 5). That is, the line L connecting the apples of the ridges 43' becomes wavy as a result of the contraction of the elastic members 45. Such a wavy shape reduces the contact area with the skin to prevent heat and humidity from being built up inside, giving a wearer dryness and comfort.

The fiber aggregate 50 and the fiber aggregate layers 52 and 53 can be made of the same materials as for the above-described sheet 44 making the elastically extensible portion. The pitch P of the ridges 43' (see FIG. 6) in their relaxed state is preferably 0.5 to 5.0 mm, particularly 1.0 to 2.0 mm. The width We of the ridges 43' in their relaxed state is preferably 0.5 to 5.0 mm, particularly 1.0 to 2.0 mm.

The absorbent articles according to the present invention are not limited to the above-described embodiments, and various changes and modifications can be made without departing from the spirit and scope of the present invention. For example, the present invention is applicable to adult incontinence pads, panty liners, and the like as well as sanitary napkins.

The ridges in the first aspect of the invention may be formed along the longitudinal direction of the elastically extensible portion 40. Such a configuration can easily be formed by, for example, bonding an elastic member of sheet form with a prescribed width in its widthwise and lengthwise stretched state to the sheet 44 discretely in the width direction. On relaxing the elastic member, there will be formed a plurality of ridges extending in the longitudinal directions. In this embodiment, the number of ridges parallel to the longitudinal direction in each elastically extensible portion 40 can be, for example, 1 to 5. Where the ridges are provided across the elastically extensible portion 40 as in the embodiment shown in FIG. 1, 5 to 50 elastic members can be disposed in each elastically extensible portion 40. The ridges across the width of the elastically extensible portion 40 do not always cross at right angles and may have some angle. Where the ridges are provided along the longitudinal direction, the width of joint areas, the interval of joint areas, the height of the ridges, and so forth are the same as those in the embodiment in which the ridges are formed across the width.

In the second aspect of the invention, the number of the ridges is, for example, 20 to 200 in each elastically extensible portion. The ridges across the width may have some angle with the width direction as far as is consistent with the effects of the second aspect of the invention. The ridges of the second aspect of the invention may be or may not be hollow. The fiber aggregate containing the elastic members may be an integral sheet made of elastic fibers.

Figure 9A:
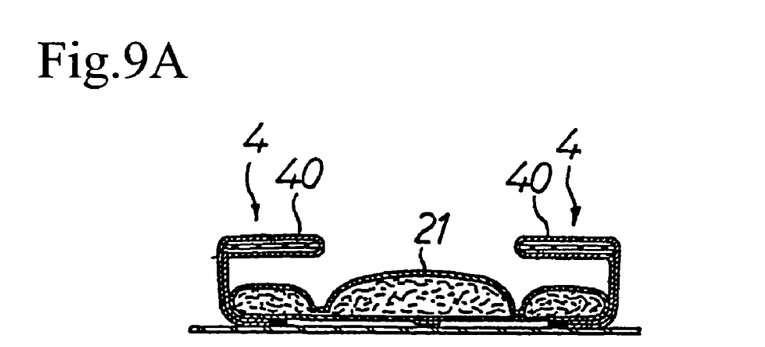
FIGS. 9A and 9B are a cross sectional views of a sanitary napkin as another embodiment of the first and second aspects of the invention.
Figure 9B:
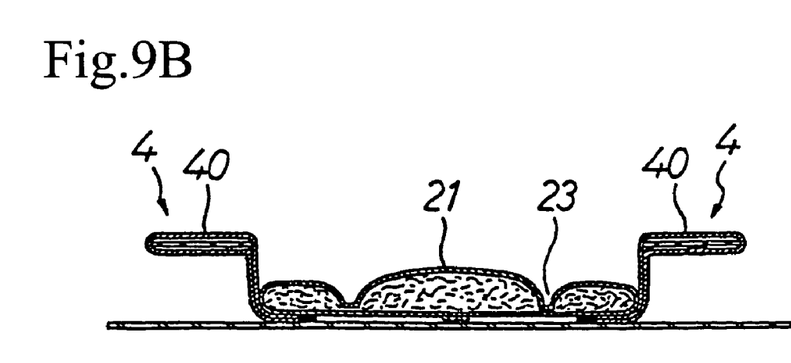

The standing gathers in the first and second aspects of the invention may have the shapes shown in FIGS. 9A and 9B. While the elastic member 45 is preferably a string with a thickness of 0.1 to 0.5 mm, particularly 0.2 to 0.4 mm, elastic members of other forms, such as bands and films, can also be used.

The elastically extensible portion on each side does not always need to provide a planar contact with the wearer's skin over its entire surface.

EXAMPLE 1

(1) Preparation of Elastically Extensible Member for Making Standing Gathers

Suction heat-bonded nonwoven fabric having a basis weight of 22 g/m$^2$ was prepared by carding of core/sheath conjugate fiber having a polyethylene terephthalate (PET) core and a polyethylene (PE) sheath and having a thickness of 2.2 dtex. Six elastic strings of polyurethane having a thickness of 470 dtex were arranged at a 4 mm interval on the middle of the nonwoven fabric at their 40% extension (in the state extended 1.4 times the original length). A styrene-butadiene copolymer-based hot-melt adhesive had previously been applied to a 150 mm length of the elastic strings at an extension of 40% in an amount of 0.07 g per meter of the string. The arrangement of the elastic strings was as shown in FIG. 4, except for the pattern of the adhesive applied and the number of the elastic members.

The nonwoven fabric on each side of the area where the elastic members were disposed was folded back to envelope the elastic members so as to have the vertical profile shown in FIG. 7A. The folded nonwoven fabric having the elastic members enveloped therein was heat embossed through the rolls of an embossing machine as shown in FIGS. 7A and 7B to be corrugated. The embossing machine had an anvil roll (upper roll) made of rubber and a metallic engraved embossing roll (lower roll). The metallic embossing roll was heated at 100° C. The embossing pressure was 4 kg/cm$^2$. The resulting elastically extensible member had a corrugated profile, taken in its longitudinal direction, as shown in FIG. 6.

(2) Preparation of Sanitary Napkin

A sanitary napkin having the structure shown in FIGS. 1 and 2, except that the elastically extensible portion had the structure shown in FIGS. 5 and 6, was prepared by using the elastically extensible member obtained in (1) above. All the materials used except the standing gathers were the same as used in Laurier Superguard (trade name) available from Kao Corp.

The resulting sanitary napkin had standing gathers having a T-shaped vertical profile along both longer sides thereof as shown in FIGS. 5 through 8. The upper and lower nonwoven cloth layers of the elastically extensible portion were both raised toward the same direction. The density of the two nonwoven cloth layers (fiber aggregate) in the valleys 51 in accordance with the corrugated profile of the embossing roll was 0.1 g/cm$^3$, and that in the ridges 43' formed between the adjacent valleys 51 was 0.05 g/cm$^3$. The pitch P of the ridges 43' was 2 mm, and the width We of the ridges 43' was 1 mm.

The sanitary napkin had an anti-leak channel 23 as shown in FIG. 1. The elastically extensible portion of the standing gathers had a width of 20 mm and a length of 150 mm. The sanitary napkin had a wing on each side thereof as shown in FIG. 1. A pressure-sensitive adhesive was applied to the back side of the napkin with which to be fixed to a garment.

EXAMPLE 2

A sanitary napkin was prepared in the same manner as in Example 1, except that the standing gathers had an inverted L-shaped vertical profile with only an outer extension as an elastically extensible portion as shown in FIG. 9B. The elastically extensible portion was 18 mm wide and 140 mm long. The elastically extensible portion had the same raised pattern as in Example 1.

Comparative Example 1

A commercially available sanitary napkin Laurier Superguard, available from Kao Corp., having the following specifications was tested as Comparartive Example 1.
Cross-section: FIG. 9B (the standing gathers have an inverted L-shaped profile).
Material and structure of elastically extensible portions: three-layer structure of nonwoven fabric/elastic member of film form/nonwoven fabric; the nonwoven fabric is the same as used in Examples 1 and 2; the elastic member is film of polyurethane. No embossing. Irregular unevenness due to contraction of the elastic member.
Dimension of standing gathers: 18 mm wide (at the elastically extensible portion); 140 mm long.

Comparative Example 2

A commercially available sanitary napkin SOPHY ACTIVE SUPPORT ULTRA (for night), produced by Uni-Charm Corp., was tested as Comparative Example 2.

The sanitary napkins prepared in Examples 1 and 2 and Comparative Examples 1 and 2 were tested as follows. The results obtained are shown in Table 1 below.

1) Soft Feel

Twenty female testers organoleptically scored the feel of the standing gathers, particularly the elastically extensible portions, of the sanitary napkins according to the following standard. An average of the scores given by the 20 tester was calculated.

Standard of evaluation:
5 . . . Very soft
4 . . . Soft
3 . . . Medium
2 . . . Slightly hard
1 . . . Hard 2) Absorbing Performance and Leakproofing Effect 2-1) Absorption at Leak A sanitary napkin was attached to a sanitary garment and fitted to a movable female body model. While the model was being made to take a walking movement of 100 steps/min (corresponding to a walking speed of 50 m/min), 1 g portions of defibrinated horse blood (available from Nippon Biotest Lab.) were poured into the napkin through a tube for every 3 minutes until the napkin began to leak. The absorption until a leak occurred was measured as "an absorption at leak". Triplicate samples were tested to obtain an average absorption at leak.

2-2) Absorption at Gather Soiling

Every time 1 g of defibrinated horse blood was poured in the measurement of absorption at leak, the garment was carefully half pulled down to see if the skin contact side of the standing gathers was soiled with blood. The amount of horse blood that had been poured when the skin contact side of the gathers were found soiled was taken as "an absorption at gather soiling".

2-3) Leakproofness

The difference obtained by subtracting "absorption at gather soiling" from "absorption at leak" was taken as an indication of the leakproofness of the standing gathers. The greater the difference, the higher the leakproofing effect.

3) Widthwise Deformation of Gathers

The width of the elastically extensible portion of the standing gathers was measured at the start of the test of absorbing performance (initial width) and at the time when a leak occurred (width at leak). A deformation ratio was calculated from equation.

Deformation ratio (%)=[(initial width−width at leak)/initial width]×100

TABLE 1

|  | Example | | Comparative Example | |
| --- | --- | --- | --- | --- |
|  | 1 | 2 | 1 | 2 |
| Softness | 4 | 4 | 3 | 2 |
| Deformation ratio (%) | 6 | 10 | 30 | 30 |
| Absorption (g) | | | | |
| at leak | 23 | 22 | 21 | 17 |
| at gather soiling | 17 | 17 | 17 | 14 |
| Leakproofness | 6 | 5 | 4 | 3 |

It is seen that the absorbent articles according to the second aspect of the invention feel soft on the skin contact side of the standing gathers and exhibit excellent planar shape retention at the elastically extensible portion thereof which is brought into contact with the wearer's skin to provide an excellent fit and high leakproofness.

The present invention provides absorbent articles, such as sanitary napkins, incontinence pads, and panty liners, which have secure soft ridges on the side to be brought into contact with the skin, feel comfortably soft at the standing gathers, and provide a good fit and leakproofness.

The present invention also provides absorbent articles, such as sanitary napkins, incontinence pads, and panty liners, which feel comfortably soft at the standing gathers, exhibit excellent planar shape retention in the elastically extensible portion giving a planar contact with the wearer's skin, and provide a good fit and leakproofness.

This application claims the priority of Japanese Patent Application Nos. 2001-19330 filed Jan. 29, 2001 and 2001-380693 filed Dec. 13, 2001, which are incorporated herein by reference.

What is claimed is:

1. An absorbent article having a liquid-retentive absorbing layer, a liquid-impermeable leakproof layer, and standing gathers on each side of said article which have an upright portion and an elastically extensible portion coming into planar contact with a wearer's skin while worn, each elastically extensible portion being substantially parallel to said absorbing layer and each upright portion extending between a portion near a corresponding longer side edge of said absorbing layer and a corresponding one of said elastically extensible portions before being worn, wherein each elastically extensible portion is made of a sheet and at least one elastic member, said elastic member being fixed to said sheet, while such is planar, discretely in the longitudinal direction thereof in its stretched state, and the parts of said sheet where said elastic member is not fixed are raised by contraction of said elastic member to form a plurality of hollow ridges parallel to each other on a side of said elastically extensible portion to be brought into contact with the wearer's skin in a linear manner along the contraction direction of said elastic member, said hollow ridges each extending across the contraction direction of said elastic member; wherein said absorbent article is substantially oblong, said standing gathers are provided along the respective longer sides of said absorbent article, and said plurality of ridges are a large number of ridges formed across a width of a corresponding one of said elastically extensible portions;

wherein each upright portion is directly attached to a middle in a width direction of a corresponding one of said elastically extensible portions.

2. The absorbent article according to claim 1, wherein said absorbent article is fixable to underwear in use.

* * * * *